(12) United States Patent
Dams et al.

(10) Patent No.: US 11,008,278 B1
(45) Date of Patent: May 18, 2021

(54) METHODS OF MAKING BENZOPHENONYL(ALK)ACRYLIC ESTERS AND SUBSTITUTED BENZOPHENONYL(ALK)ACRYLIC ESTERS IN FLOW REACTORS

(71) Applicant: 3M INNOVATIVE PROPERTIES COMPANY, St. Paul, MN (US)

(72) Inventors: Rudolf J. Dams, Antwerp (BE); Rudy W. Van Campenhout, Hoboken (BE)

(73) Assignee: 3M Innovative Properties Company, St. Paul, MN (US)

( * ) Notice: Subject to any disclaimer, the term of this patent is extended or adjusted under 35 U.S.C. 154(b) by 32 days.

(21) Appl. No.: 16/499,963

(22) PCT Filed: Jun. 7, 2018

(86) PCT No.: PCT/US2018/036372
§ 371 (c)(1),
(2) Date: Oct. 1, 2019

(87) PCT Pub. No.: WO2018/231610
PCT Pub. Date: Dec. 20, 2018

Related U.S. Application Data

(60) Provisional application No. 62/518,017, filed on Jun. 12, 2017.

(51) Int. Cl.
*C07C 67/14* (2006.01)

(52) U.S. Cl.
CPC .................................... *C07C 67/14* (2013.01)

(58) Field of Classification Search
CPC ...................................................... C07C 67/14
See application file for complete search history.

(56) References Cited

U.S. PATENT DOCUMENTS

| | | | |
|---|---|---|---|
| 6,192,596 | B1 | 2/2001 | Bennett |
| 6,228,434 | B1 | 5/2001 | Affinito |
| 6,449,184 | B2 | 9/2002 | Kato |
| 10,308,584 | B2 * | 6/2019 | Dams ..................... B01J 19/248 |
| 2019/0010268 | A1 * | 1/2019 | Zhang ....................... C08F 2/38 |

FOREIGN PATENT DOCUMENTS

| | | | |
|---|---|---|---|
| WO | WO 2017-030950 | 2/2017 | |
| WO | WO-2017030950 A1 * | 2/2017 | ............ C08F 220/30 |
| WO | WO 2017-147040 | 8/2017 | |
| WO | WO-2017147040 A1 * | 8/2017 | ............. C07C 67/14 |

OTHER PUBLICATIONS

Chevalier, et al., "Microreactors for industrial multi-phase applications; Test reactions to develop innovative glass microstructure designs," Chemistry Today, vol. 26, No. 2, Mar.-Apr. 2008, pp. 38-42.
Wiles, "Recent Advances in Micro Reaction Technology"; Chemical Communications; 2011, vol. 47, No. 23, pp. 6512-6535.
International Search Report for PCT International Application No. PCT/US2018/036372, dated Sep. 20, 2018, 6 pages.

\* cited by examiner

*Primary Examiner* — Yevgeny Valenrod
*Assistant Examiner* — Blaine G Doletski
(74) *Attorney, Agent, or Firm* — Eric E. Silverman

(57) ABSTRACT

A method of making a benzophenonyl (alk)acrylic ester comprising adding to a mixing chamber of a microflow reactor a benzophenone alcohol, a benzophenone alcohol or substituted benzophenone alcohol comprising at least one hydroxy moiety, one or more bases, a polar liquid, an (alk)acryloyl halide or 3-haloalkylcarboxyl halide, and an organic liquid that is immiscible with the polar liquid; and producing a product stream comprising one or more benzophenonyl (alk)acrylic esters and one or more salts of the one or more bases; wherein the product stream has an organic portion and a polar portion, the organic portion of the product stream comprising the benzophenonyl (alk)acrylic ester, unreacted benzophenone alcohol or substituted benzophenone alcohol, and organic byproducts in the product stream; and further wherein either (a) the organic liquid comprises a compound of Formula (I); or (b) the method further comprises adding a compound of Formula (I) to the product stream; or (c) the organic liquid comprises a compound of Formula (I) and the method further comprises adding a compound of Formula (I) to the product stream (I) wherein $R_1$ is H or $C_1$ to $C_4$ alkyl; and $R_2$ is $C_1$ to $C_{12}$ alkyl optionally interrupted by one or more O atoms.

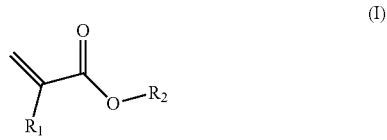

(I)

15 Claims, No Drawings

METHODS OF MAKING BENZOPHENONYL(ALK)ACRYLIC ESTERS AND SUBSTITUTED BENZOPHENONYL(ALK)ACRYLIC ESTERS IN FLOW REACTORS

CROSS REFERENCE TO RELATED APPLICATIONS

This application is a national stage filing under 35 U.S.C. 371 of PCT/US2018/036372, filed Jun. 7, 2018, which claims the benefit of U.S. Application No. 62/518,017, filed Jun. 12, 2017, the disclosure of which is incorporated by reference in its/their entirety herein.

BACKGROUND (Alk)acrylic esters have a wide variety of uses, such as monomers or co-monomers for making a wide variety of polymers. (Alk)acrylic esters can be produced industrially, such as by esterification of an alcohol by an (alk)acrylic acid under azeotropic conditions wherein water is removed from the reaction mixture during the reaction by distillation. This method is not useful for the manufacture of all (alk)acrylic esters, particularly those that are unstable at higher temperatures.

(Alk)acrylic esters can also be produced by addition of an alcohol to an (alk)acryloyl chloride. This reaction can be difficult to perform on an industrial scale because, in order to proceed in good yield, it is necessary to rigorously exclude water from the reaction. Also, the reaction is highly exothermic, and therefore requires both very slow addition of the alcohol to the (alk)acryloyl chloride and effective cooling. Even with cooling, the reaction can pose a risk of explosion or fire when performed on an industrial scale.

DETAILED DESCRIPTION

Throughout this disclosure, singular forms such as "a," "an," and "the" are often used for convenience; however, it should be understood that the singular forms are meant to include the plural unless the singular alone is explicitly specified or is clearly indicated by the context.

Some of the terms used in this application have special meanings, as defined herein. All other terms will be known to the skilled artisan, and are to be afforded the meaning that a person of skill in the art at the time of the invention would have given them.

Two or more liquids or solvents are "miscible" if they are soluble in each other in all proportions at room temperature and atmospheric pressure. Thus, two miscible liquids or solvents will form a solution when mixed in any ratio.

Two or more liquids are "immiscible" if they are not soluble in each other in all proportions at room temperature and atmospheric pressure. Immiscible liquids or solvents may still have some solubility in one another. For example, diethyl ether can form a solution in water up to about 10% by weight, but is still immiscible in water because it does not form a solution in all proportions.

"Independently," when used in reference to the identify of one or more variable elements, means that each occurrence of any of the variable elements may have the same or different identity, within the specified limitations, regardless of the identity of any other occurrence of the reference element. Thus, if there are two occurrences of element "E," and element E can be independently selected from identity Y or identity Z, each of the two occurrences of E can be either Y or Z, in any combination (e.g., YY, YZ, ZY, or ZZ).

"Alkyl" refers to an aliphatic hydrocarbon radical. Alkyl radicals can have any number of carbon atoms; the number of carbon atoms is often denoted in this disclosure by the notation "Cn" wherein "n" is an integer that corresponds to the number of carbon atoms. Thus, C1 means one carbon atom, C2 means two carbon atoms, C3 means three carbon atoms, etc. Typical alkyl groups are C30 or less, such as C26 or less, C24 or less, C22 or less, C20 or less, C18 or less, C16 or less, C14 or less, C12 or less, C10 or less, C8 or less, C6 or less, C4 or less, or C2 or less. Some alkyl groups are C1. Typical alkyl groups are C2 or greater, C4 or greater, C6 or greater, C8 or greater, C10 or greater, C12 or greater, C14 or greater, C16 or greater, C18 or greater, C20 or greater, C22 or greater, C24 or greater, C26 or greater, or C28 or greater. Exemplary alkyl groups include methyl, ethyl, propyl, isopropyl, n-butyl, t-butyl, sec-butyl, iso-butyl, cyclohexyl, cyclopentyl, 2-ethyl hexyl, iso-octyl, n-octyl, dodecyl, hexadecyl, behenyl, and the like.

"Alcohol" refers to compounds having a hydroxy radical or a deprotonated hydroxy radical.

"Halide" and other forms thereof, such as "halo," are used to refer to a chloride, bromide, or iodide radical. Halides as used herein are most commonly chloride.

"Hydroxy" refers to an OH radical.

"Aryl" refers to a fully conjugated, cyclic, hydrocarbon mono radical. Examples of aryl radicals include phenyl, naphthyl, and the like.

"Arylene" refers to a fully-conjugated cyclic, hydrocarbon di radical. Examples of arylene radicals include phenylene, naphthylene, and the like. Each of the diradicals in a substituted aryl can be located on the conjugated ring or on the substituent.

"Substituted aryl" refers to an aryl mono radical wherein one or more of the hydrogen atoms are substituted with a substituent. Typical substituents include alkyl, alkenyl, oxyalkyl, hydroxy, and the like. Exemplary substituted aryl groups include toluyl, xylyl, hydroxy aryl, alkyl hydroxy aryl, and the like.

"Carboxyl" refers to the C(O) diradical.

"Carboxyl halide" refers to the carbon centered radical O=C—X, wherein X is halide.

"Alkylcarboxyl halide" refers to a compound featuring a chemical bond between an alkyl radical of at least two carbon atoms and a carboxyl halide.

"3-Haloalkylcarboxyl halide" refers to an alkylcarboxyl halide bearing a halide radical that is covalently bonded to a carbon atom in the 3-position, i.e., the carbon atom in the beta position with respect to the carbonyl. The alkyl group is often a C2 alkyl group, in which case the 3-haloalkylcarboxyl halide is a 3-halopropionyl halide, such as 3-chloropropionyl halide or 3-chloropropionyl chloride. The alkyl group in a 3-haloalkylcarboxyl halide can be substituted or unsubstituted; when substituted, however, there is at least one hydrogen atom bound to the carbon in the 2 position, i.e., the carbon atom in the alpha position with respect to the carbonyl. Typical substituents include alkyl, oxyalkyl, oxyalkyloxyalkyl, ether, aryl, heteroaryl, alkaryl, alkheteroaryl, oxyaryl, oxyheteroaryl, arylalkyl, heteroarylalkyl, oxyarylalkyl, oxyhetetroarylalkyl, and the like. The alkyl group in 3-haloalkylcarboxyl halide can also be unsubstituted, which is more common.

"Acryloyl halide" means acryloyl chloride, acryloyl bromide, or acryloyl iodide. "(Alk)acryloyl halide means an acryloyl halide or an acryloyl halide bearing an alkyl radical covalently bonded to the carbon atom in the 3-position, i.e., the carbon atom in the beta position with respect to the carbonyl.

"Benzophenonyl" and "substituted benzophenonyl" refers to mono-radical of benzophenone or substituted benzophenone, respectively. The benzophenonyl radical has the chemical structure $C_6H_4C(O)C_6H_5$. The radical can be centered on any carbon of the aryl ring (but not on the carbonyl carbon), though it is most frequently at the 4-position. A substituted benzophenonyl is typically substituted with alkyl or oxyalkyl, but can also be substituted with aryl, substituted aryl, oxyaryl, substituted oxyaryl, heteroaryl, oxyheteroaryl, alkenyl, hydroxy, or the like. When a substituent is alkyl, it is most commonly methyl, ethyl, propyl, isopropyl, n-butyl, t-butyl, sec-butyl, iso-butyl, cyclohexyl, cyclopentyl, 2-ethyl hexyl, iso-octyl, n-octyl, dodecyl, hexadecyl, or behenyl. When a substituent is oxyalkyl, it is most commonly oxymethyl, oxyethyl, oxypropyl, oxyisopropyl, oxyn-butyl, oxyt-butyl, oxysec-butyl, oxyiso-butyl, oxycyclohexyl, oxycyclopentyl, oxy2-ethyl hexyl, oxyiso-octyl, oxyn-octyl, oxydodecyl, oxyhexadecyl, or oxybehenyl. When a substituent is aryl, it is most commonly phenyl or naphthyl. When a substituent is oxyaryl, it is most commonly oxyphenyl or oxynapthtyl. When a substituent is substituted aryl, it is most commonly toluyl or xylyl. When a substituent is substituted oxyaryl, it is most commonly oxytoluyl or oxyxylyl. When a substituent is heteroaryl, it is most commonly furanyl or pyridinyl. Hydroxy substituents are also possible. The substituent can be on any position, but is most often in the 4' position, especially when the radical is centered on the 4 position.

"Benzophenone alcohol" and "substituted benzophenone alcohol" refer to a chemical compound having the formula $HO—C_6H_4—C(O)—C_6H_5$, or a substituted version thereof, respectively. The alcohol moiety can be centered on any aryl carbon, but is most often on the 4 carbon. When substituted, the benzophenone alcohol is typically substituted with alkyl or oxyalkyl, but can also be substituted with aryl, substituted aryl, oxyaryl, substituted oxyaryl, heteroaryl, oxyheteroaryl, alkenyl, hydroxy, or the like. When a substituent is alkyl, it is most commonly methyl, ethyl, propyl, isopropyl, n-butyl, t-butyl, sec-butyl, iso-butyl, cyclohexyl, cyclopentyl, 2-ethyl hexyl, iso-octyl, n-octyl, dodecyl, hexadecyl, or behenyl. When a substituent is oxyalkyl, it is most commonly oxymethyl, oxyethyl, oxypropyl, oxyisopropyl, oxyn-butyl, oxyt-butyl, oxysec-butyl, oxyiso-butyl, oxycyclohexyl, oxycyclopentyl, oxy2-ethyl hexyl, oxyiso-octyl, oxyn-octyl, oxydodecyl, oxyhexadecyl, or oxybehenyl. When a substituent is aryl, it is most commonly phenyl or naphthyl. When a substituent is oxyaryl, it is most commonly oxyphenyl or oxynapthtyl. When a substituent is substituted aryl, it is most commonly toluyl or xylyl. When a substituent is substituted oxyaryl, it is most commonly oxytoluyl or oxyxylyl. When a substituent is heteroaryl, it is most commonly furanyl or pyridinyl. Hydroxy substituents are also possible. The substituent can be on any position, but is most often in the 4' position, especially when the radical is centered on the 4 position. Suitable benzophenone alcohols or substituted benzophenone alcohols include 4-hydroxy benzophenone, 4-hydroxyethyl benzophenone, 2-hydroxybenzophenone, 3-hydroxybenzophenone, 4-chloro 4'-hydroxy benzophenone, 5-bromo 2-hydroxybenzophenone, 5-chloro 2-hydroxybenzophenone, and the like. Most commonly, the benzophenone alcohol is 4-hydroxy benzophenone.

A "benzophenonyl (alk)acrylic ester" is the ester condensation product of a benzophenone alcohol and an (alk) acrylic ester.

A "substituted benzophenonyl (alk)acrylic ester" is the ester condensation product of a substituted benzophenone alcohol and a substituted (alk)acrylic ester.

The "molar flow ratio" of two substances is the ratio of the flow rates of the two substances in mols of substance per unit time. A molar flow ratio can be calculated by one of ordinary skill in the art by dividing the concentration, in molarity, of each substance by its flow rate and then determining the ratio of the two resulting values. For example, if substance "X" is present in a liquid at a concentration of 2 mmol/mL and is flowing at a rate of 1 mL/min and substance "Y" is present in a liquid at a liquid at a concentration of 4 mmol/mL and is flowing at a rate of 2 mL/min, then the molar flow ratio of X to Y is 1 to 1 (i.e. ((2 mmol/mL of X)/(1 mL of X/min)):((4 mmol/mL of Y)/(2 mL of Y/min)). When the molar flow ratio refers in part to an acid, a base, or an alcohol, then the moles of base are considered to be the moles of acidic or basic equivalents. For example, if $Ca(OH)_2$ is present in a liquid at a concentration of 2 mmol/mL and is flowing at a rate of 1 mL/min, and an alcohol is present in a liquid at a concentration of 4 mmol/ mL and is flowing at a rate of 2 mL/min, then the molar flow ratio of the $Ca(OH)_2$ to the alcohol is 2 to 1 (i.e., (2 mmol/mL of $Ca(OH)_2$×2 moles OH/mol $Ca(OH)_2$)/(1 mL $Ca(OH)_2$/min)):((4 mmol/mL of Y)/(2 mL of Y/min)). Molar flow ratio is sometimes expressed as "N to at least M," wherein N and M are values. This notation means that the value M can be the stated value or greater. Thus, if the molar flow ratio of X to Y is "1 to at least 1," then the molar flow ratio can be 1 to any value that is 1 or greater, e.g., 1 to 1, 1 to 1.5, 1 to 2, 1 to 10, etc.

A benzophenonyl (alk)acrylic ester or substituted benzophenonyl (alk)acrylic ester can be made by a chemical reaction that takes place within the mixing chamber of a microflow reactor. A benzophenone alcohol or substituted benzophenone alcohol, one or more bases that are sufficient to at least partially deprotonate the phenyl alcohol or substituted phenyl alcohol, a polar liquid, an (alk)acryloyl halide or 3-haloalkylcarboxyl halide, and an organic liquid that is immiscible with the polar liquid and present in sufficient quantity to dissolve the (alk)acryloyl halide or 3-haloalkylcarboxyl halide can be added to the microreactor as the ingredients for this reaction.

Any microflow reactor can be used. Typically, the microflow reactor will have at least a first addition port and a second addition port for adding liquids to the mixing chamber of the microflow reactor. In many cases, further addition ports can be present. In many cases, only two, three, or four addition ports are used for adding materials to the mixing chamber. When there are unused addition ports, the unused addition ports will typically be plugged so as to prevent or mitigate intake of any unwanted substances from outside the mixing chamber and loss of reactants or products from the mixing chamber. One of more of the addition ports can have a check valve to prevent backflow, but this is not necessary in most cases because the pressure of the reactant stream through the addition port is usually sufficient to prevent backflow. The mixing chamber of the microflow reactor will also typically have at least one exit port for a product stream to exit.

Some microflow reactors will have a mixing chamber with an internal volume of no more than 10 mL, such as no more than 5 mL, no more than 0.9 mL, no more than 0.8 mL, no more than 0.75 mL, no more than 0.6 mL, no more than 0.5 mL, no more than 0.4 mL, no more than 0.3 mL, no more than 0.25 mL, no more than 0.1 mL, or no more than 0.05 mL. The microflow reactor typically has a mixing geometry for promoting mixing of the ingredients that are added to the mixing chamber. In many cases, the mixing chamber can be designed to create a flowing plug of ingredients such that back-mixing of materials in the microflow reactor with materials later added to the microflow reactor is mitigated. The mixing chamber can have any suitable geometry, such as T-shape, star-shape, circuitous tube shape, and the like. Suitable microflow reactors are commercially available, for example, under the trade designations IDEX 91 (ACHROM, Belgium) and LABTRIX START 1805-L-2 (Chemtrix BV, UK), the latter of which can be fitted with a glass microchip, such as those available under the trade designation TPE 3223 (Chemtrix BV), which can function as a mixing chamber. Other microflow reactors have been described, for example, in U.S. Pat. Nos. 6,449,184, 6,228,434, and 6,192,596.

Impinging flow microreactors can be used. Such reactors are designed with addition ports that direct reactant streams to meet in a volume of the impinging flow reactor where they form a product stream. In such a case, the volume of the impinging flow reactor where the reactant streams meet is the mixing chamber. The pressure of the reactant streams through the inlet ports pushes the product stream through the mixing chamber and out of the exit port.

Any benzophenone alcohol or substituted benzophenone alcohol can be used, so long as it contains at least one hydroxy radical that is capable of reacting with an (alk) acryloyl chloride, such as acryloyl chloride or methacryloyl chloride, or with a 3-haloalkylcarboxyl halide, such as 3-halopropionyl halide, 3-chloropropionyl halide, or 3-chloropropionyl chloride, under the reaction conditions.

In most cases, a benzophenone alcohol is used. The most common benzophenone alcohol is 4-hydroxy benzophenone. Most often only a single benzophenone alcohol or substituted benzophenone alcohol is used, and no other alcohols that react under the reaction conditions to form esters are included. This is most common because, typically, the desired product is a single benzophenonyl (alk)acrylic ester or substituted benzophenonyl (alk)acrylic ester. However, it is also possible to use a mixture of more than one benzophenone alcohol. In such cases, the products will be a mixture of (alk)acrylic esters, at least one of which is a phenyl having different ester portions. The molar ratio of the different products will usually be similar to the molar ratio of the alcohols that are added to the mixing chamber of the microflow reactor. Making more than one (alk)acrylic ester, at least one of which is a benzophenonyl (alk)acrylic ester or substituted benzophenonyl (alk)acrylic ester, at the same time in the same microflow reactor can be useful, for example, when the resulting mixture is to be polymerized together into a single copolymer. In such a case, the product stream can exit the microflow reactor, typically through an exit port, to form a product stream that can be fed into another reactor, either directly or after separation of water, for example, a reactor for polymerizing the mixture of products.

The hydroxy benzophenone or substituted hydroxy benzophenone can be any suitable hydroxy benzophenone or substituted hydroxy benzophenone. Suitable hydroxy benzophenones or substituted hydroxy benzophenones are those that can react with an (alk)acryloyl chloride, such as acryloyl chloride or methacryloyl chloride, or with a 3-haloalkycarboxyl halide, such as 3-halopropionyl halide, 3-chloropropionyl halide, or 3-chloropropionyl chloride, to form a (alk)acrylic ester under the reaction conditions. Examples include 4-hydroxy benzophenone, alkyl substituted 4-hydroxy benzophenone, aryl substituted 4-hydroxy benzophenone, and the like. 4-hydroxy benzophenone is most commonly employed.

The one or more bases can be any bases that are sufficient to at least partially deprotonate the benzophenone alcohol. Typically, the one or more bases includes an amine base. Common amine bases include triethyl amine, dimethylethyl amine, trimethyl amine, methyldiethyl amine, and the like. Triethyl amine is the most commonly used amine base. Alkali metal hydroxides, such as sodium hydroxide or potassium hydroxide, can also be used, either by themselves or in combination with an amine base, such as triethyl amine. Alkali earth metal hydroxides, such as calcium hydroxide, can also be used although this is less common.

The polar liquid is commonly water, most often deionized water. Other solvents are occasionally used. When the solvent is not water, it is typically not an alcohol or any other solvent that reacts with one of the reactants, since such solvents could take part in the reaction. An alcohol can be used as both the polar liquid and as a reactant in some cases, particularly when two alcohols are used one of which being the phenyl alcohol and the other being a liquid alcohol. In such cases, the liquid alcohol is often mixed with water.

In most cases, the polar liquid will dissolve all or part of the one or more bases. Most commonly, the polar liquid will dissolve all of the one or more bases. This is particularly the case when the one or more bases are not liquids at the reaction temperature, which is typically room temperature. Thus, in most cases, the one or more bases will be added to the mixing chamber of the microflow reactor as a solution in the polar liquid, which is most often water. The most commonly used bases, alkali metal hydroxides and triethanol amine, are highly water soluble and therefore can be added to the mixing chamber of the microflow reactor in this manner. When a base is also soluble in the organic liquid, then it is possible to add that base to the mixing chamber of the microflow reactor as a solution in the organic liquid. When a base is liquid at the reaction temperature, which is typically room temperature, then it is also possible to add that base to the mixing chamber of the microflow reactor neat, although this is not typical.

The benzophenone alcohol or substituted benzophenone alcohol, plus any other alcohols that may be present, react with at least one of (alk)acryloyl halide or 3-haloalkylcarboxyl halide inside the mixing chamber of the microflow reactor. In some cases, both of (alk)acryloyl halide and 3-haloalkylcarboxyl halide can be used, but this is not common.

When an (alk)acryloyl halide is used, it is often an acryloyl halide. When an alkyl group is present, the alkyl group can be any alkyl group. Most commonly, the alkyl group is C10 or less, such as C9 or less, C8 or less, C7 or less, C6 or less, C5 or less, C4 or less, C3 or less, C2 or less, or C1. The alkyl group is most often methyl. Thus, the most common (alk)acryloyl halides are acryloyl halide and methacryloyl halide, in particular acryloyl chloride and methacryloyl chloride.

When 3-haloalkylcarboxyl halide is used, the alkyl can be any suitable alkyl. Most commonly the alkyl group is C10 or less, such as C9 or less, C8 or less, C7 or less, C6 or less, C5 or less, C4 or less, C3 or less, or C2. In many cases, the 3-haloalkylcarboxyl halide is 3-halopropionyl halide, such as 3-halopropionyl chloride, 3-chloropropionyl halide, or 3-chloropropionyl chloride. 3-chloropropionyl chloride is most common.

The organic liquid is typically suitable for dissolving most if not all of the (alk)acryloyl halide or 3-haloalkylcarboxyl halide as well as most if not all of the reaction product. In addition, the phenyl alcohol typically has some solubility in the organic liquid in order to facilitate reaction with the (alk)acryloyl halide or 3-haloalkylcarboxyl halide. The organic liquid can also be suitable for dissolving all or some of the at least one base, but this is not necessary.

The organic liquid is conveniently immiscible with the polar liquid. This immiscibility facilitates separation of the phenyl or substituted phenyl (alk)acryl ester product, which is typically present largely in the organic liquid, from salts and other polar liquid soluble byproducts. Because the polar liquid is typically water, the organic liquid is typically immiscible with water. Exemplary organic liquids include dichloromethane, ethyl acetate, butyl acetate, methyl ethyl ketone, methyl butyl ketone, and the like. (Alk)acrylic esters that are immiscible with water can also be used.

In practice, the materials described herein are added to the mixing chamber of a microflow reactor. The addition is typically through at least two of the addition ports. Thus, the benzophenone alcohol or substituted benzophenone alcohol is typically added through a first addition port and the (alk)acryloyl halide or 3-haloalkylcarboxyl halide is typically added through a second addition port. Adding the benzophenone alcohol or substituted benzophenone alcohol through a different port than the (alk)acryloyl halide or 3-haloalkylcarboxyl halide prevents those reactants from undergoing a chemical reaction outside of the mixing chamber.

Most commonly two addition ports are used. In such cases, the polar liquid, such as water, one or more bases, such as triethyl amine, alkali metal hydroxide, or both, and alcohol are typically added together through the first port. The mixture is most commonly added in the form of a solution wherein the one or more bases and alcohol are dissolved in the polar liquid. The (alk)acryloyl halide or 3-haloalkylcarboxyl halide and the organic liquid are typically added through the second addition port. Typically, the (alk)acryloyl halide or 3-haloalkylcarboxyl halide is added as a solution in the organic liquid.

Three or four addition ports can also be used. When three addition ports are used, the benzophenone alcohol or substituted benzophenone alcohol, one or more bases, and polar liquid can be added, typically as a solution, through the first addition port, the (alk)acryloyl halide or 3-haloalkylcarboxyl halide can be added through a second addition port, and the organic liquid can be added through a third addition port. Alternatively, the benzophenone alcohol or substituted benzophenone alcohol can be added through the first addition port, the polar liquid can be added through the second addition port, and the (alk)acryloyl halide or 3-haloalkylcarboxyl halide can be added, typically as a solution, through the third addition port. When four addition ports are used, the benzophenone alcohol or substituted benzophenone alcohol and one or more bases can be added through the first addition port, the (alk)acryloyl halide or 3-haloalkylcarboxyl halide can be added through the second addition port, the polar liquid can be added through the third addition port, and the organic liquid can be added through the fourth addition port.

Other variations are also possible when three or more addition ports are used. In one such variation, the benzophenone alcohol or substituted benzophenone alcohol can be added in the organic liquid rather than in the polar liquid. In one example of this variation, the benzophenone alcohol or substituted benzophenone alcohol can be added as a solution in a first organic liquid through the first addition port, the (alk)acryloyl halide or 3-haloalkylcarboxyl halide can be added as a solution in a second organic liquid through the second addition port, and the one or more bases can be added as a solution in the polar liquid, typically water, through the third addition port. The first and second organic liquids can be the same or different, and can be selected from any of the organic liquids discussed herein. Yet other variations are possible, most of which will keep the (alk)acryloyl halide or 3-haloalkylcarboxyl halide separated from the organic liquid outside of the mixing chamber to avoid unwanted chemical reactions.

The ingredients can be added to the mixing chamber of the microflow reactor at any suitable flow rate. The flow rate will vary depending on the internal volume and geometry of the mixing chamber. Exemplary flow rates are between 0.1 L/min and 10 L/min, for example greater than 0.1 L/min, greater than 0.2 L/min, greater than 0.3 L/min, greater than 0.4 L/min, greater than 0.5 L/min, greater than 0.6 L/min, greater than 0.7 L/min, greater than 0.8 L/min, greater than 0.9 L/min, greater than 1.0 L/min, greater than 1.1 L/min, greater than 1.2 L/min, greater than 1.3 L/min, greater than 1.4 L/min, greater than 1.5 L/min, greater than 1.6 L/min, greater than 1.7 L/min, greater than 1.8 L/min, greater than 1.9 L/min, greater than 2.0 L/min, greater than 2.1 L/min, greater than 2.2 L/min, greater than 2.3 L/min, greater than 2.4 L/min, greater than 2.5 L/min, greater than 2.6 L/min, greater than 2.7 UL/min, greater than 2.8 UL/min, greater than 2.9 UL/min, greater than 3.0 L/min, greater than 3.25 L/min, greater than 3.5 L/min, greater than 3.75 L/min, greater than 4.0 L/min, greater than 4.5 L/min, greater than 5.0 L/min, greater than 5.5 L/min, greater than 6.0 L/min, greater than 6.5 L/min, greater than 7.0 L/min, greater than 7.5 L/min, greater than 8.0 L/min, greater than 8.5 L/min, greater than 9.0 L/min, or greater than 9.5 L/min. Suitable flow rates can also be up to 10 L/min, up to 9.5 L/min, up to 9.0 L/min, up to 9.0 L/min, up to 8.5 L/min, up to 8.0 L/min, up to 7.5 L/min, up to 7.0 L/min, up to 6.5 L/min, up to 6.0 L/min, up to 5.5 L/min, up to 5.0 L/min, up to 4.75 L/min, up to 4.5 L/min, up to 4.25 L/min, up to 4.0 L/min, up to 3.75 L/min, up to 3.5 L/min, up to 3.25 L/min, up to 3.0 L/min, up to 2.9 L/min, up to 2.8 L/min, up to 2.7 L/min, up to 2.6 L/min, up to 2.5 L/min, up to 2.4 L/min, up to 2.3 L/min, up to 2.2 L/min, up to 2.1 L/min, up to 2.0 L/min, up to 1.9 L/min, up to 1.8 L/min, up to 1.7 L/min, up to 1.6 L/min, up to 1.5 L/min, up to 1.4 L/min, up to 1.3 L/min, up to 1.2 L/min, up to 1.1 L/min, up to 1.0 L/min, up to 0.9 L/min, up to 0.8 L/min, up to 0.7 L/min, up to 0.6 L/min, or up to 0.5 L/min. Other flow rates may also be suitable, depending on the geometry and internal volume of the microflow reactor that is used. A person of skill in the art will be able to determine appropriate flow rates from the guidance provided herein, in combination with their knowledge of the art.

Selecting appropriate molar flow ratios of some of the components can be important in achieving optimal results. The term molar flow ratio is defined herein. The inventors have found that using the correct molar flow ratios can in many cases be critical for achieving the desired products in high yield. Thus, the molar flow ratio of the benzophenone alcohol or substituted benzophenone alcohol to the sum of all of the one or more bases is typically 1 to at least 1, at least 1.5, or 1 to at least 1.7, particularly when (alk)acryloyl halide, such as (alk)acryloyl chloride or (meth)acryloyl chloride, is used. In some cases, the molar flow ratio of the benzophenone alcohol or substituted benzophenone alcohol to the sum of all of the one or more bases can be even higher, such as 1 to at least 2, 1 to at least 2.5, or even 1 to at least 2.7. Such higher molar flow ratios are not required unless otherwise specified, but they are often beneficial when 3-haloalkylcarboxyl halide is used as a reactant.

The molar flow ratio of the benzophenone alcohol or substituted benzophenone alcohol to the (alk)acryloyl halide or 3-haloalkylcarboxyl halide is typically 1 to at least 1.1. When the molar flow ratio is lower, the amount of desired product in the product stream is often unacceptably low. An even higher molar flow ratio can also be used in some cases. Thus, the molar flow ratio of alcohol to (alk)acryloyl halide or 3-haloalkylcarboxyl halide can be 1 to at least 1.2, 1 to at least 1.3, 1 to at least 1.4, 1 to at least 1.5, 1 to at least 1.6, 1 to at least 1.7, 1 to at least 1.8, 1 to at least 1.9, 1 to at least 2, 1 to at least 2.1. 1 to at least 2.2, 1 to at least 2.3, 1 to at least 2.4, or 1 to at least 2.5. Such higher molar flow ratios are not required unless otherwise specified.

When a benzophenone poly alcohol or substituted benzophenone poly alcohol having more than one hydroxy radical per molecule is used, in order to react each hydroxy radical with a molecule of the (alk)acryloyl halide or 3-haloalkylcarboxyl halide, the molar flow ratio discussed above can be used, except that the molar flow ratios would be based on mol equivalents of hydroxy radical rather than mols of poly alcohol.

In the microflow reactor, the reaction of the alcohol and (alk)acryloyl halide or 3-haloalkylcarboxyl halide typically produces one or more salts of the one or more bases. If these salts precipitate, they can clog the microflow reactor causing a process failure. Thus, the polar liquid, which is typically water, must be present in sufficient quantity to dissolve substantially all of the salts. In this context, "substantially all" means that enough salt is dissolved such that any undissolved salt does not clog the microflow reactor during the process. The flow rate necessary to achieve this result can vary greatly and depends on the volume and geometry of the particular microflow reactor that is used. Following the guidelines herein in combination with their knowledge of the art, a person of ordinary skill in the art will be able to determine a proper flow rate of polar liquid, such as water, in order to assure that all of the salts are dissolved. Thus, if salts clog the microflow reactor at a particular flow rate, the problem can be ameliorated in several ways. If the polar liquid is being added as the solvent of a solution, for example, having the benzophenone alcohol or substituted benzophenone alcohol, one or more bases, or both as solute, then the flow rate of this solution can be increased or the concentration of the solute or solutes decreased. If neither of these is feasible, for example, because of the requirement to maintain an appropriate molar flow ratio or for other reasons, then the clogging problem can be ameliorated by using more than two addition ports and adding the polar liquid, such as water, through a third or fourth addition port. By using different addition ports for the polar liquid and the benzophenone alcohol or substituted benzophenone alcohol or one or more bases, the polar liquid flow rate can be controlled, for example increased, without the need to change the flow rate of other ingredients in order to maintain the necessary molar flow ratio.

In practice, it can be desirable to rinse the microflow reactor before starting the reaction. The rinsing step can be performed again before taking the microflow reactor off line, when restarting the process after the microflow reactor has been off line, or both. Rinsing typically comprises allowing a solvent, typically the organic liquid or the polar liquid as described herein, to flow through the microflow reactor. The flow rate of the polar liquid during the rinsing step can be any suitable flow rate, which will depend on the volume of the microflow reactor. The rinsing step, when employed, is often performed for a length of time suitable to remove any salts, contaminants, or impurities that have accumulated within the microflow reactor. This time will vary depending on the volume of the microflow reactor, but is typically from 1 minute to 1 hour, and most often from 1 minute to 15 minutes. The solvent then exits the microflow reactor and can be collected from the exit port. The rinsing step is not needed in all cases.

A priming step can also be performed before starting the reaction. If both rinsing and priming steps are employed, the priming step is typically performed after the rinsing step. The priming step typically comprises pumping the benzophenone alcohol or substituted benzophenone alcohol, which can optionally be dissolved in the polar liquid or the organic liquid, through the microflow reactor, including the mixing chamber, and then collecting it after it passes through the exit port. The benzophenone alcohol or substituted benzophenone alcohol that is used in the priming step is typically discarded. The flow rate of benzophenone alcohol or substituted benzophenone alcohol during the priming step can be the same as that discussed above with respect to the addition of benzophenone alcohol or substituted benzophenone alcohol during the reaction. The priming step can be conducted for any suitable length of time, typically from 1 minute to 1 hour, such as from 1 minute to 15 minutes.

Once the any rinsing or priming steps have been completed, the ingredients can be added to the mixing chamber of the microflow reactor under the conditions described herein and allowed to mix inside the mixing chamber to form a product stream. The product stream can then exit the mixing chamber through the exit port. It is often convenient to attach tubing to the exit port. The tubing can serve one or more purposes. For example, the tubing can function to cool the reaction mixture, to allow space for the reaction to complete, to transport the product stream to a desired location, for example, to collect the product or to act as a feed for another reactor, such as another microflow reactor, or any combination of the foregoing. The various ingredients can be pumped into the reactor using any suitable pump. For small scales and short run times, syringe pumps can be used. Other pumps, such as gear pumps, multi-piston pumps, and the like, may be suitable for larger scales or longer run times. After a brief initial startup time, the (alk)acrylic ester product in the product stream will be exiting the mixing chamber of the microflow reactor through the exit port simultaneously with the addition of the ingredients through the addition ports.

Although the reaction of benzophenone alcohol or substituted benzophenone alcohol with (alk)acryloyl halide or 3-haloalkylcarboxyl halide is usually highly exothermic, it is typically not necessary to cool or otherwise adjust the temperature of the microflow reactor during the process described herein. Thus, the reaction can be carried out without any cooling of the microflow reactor, specifically without cooling the mixing chamber of the microflow reactor. Instead, the process can be carried out at room temperature without any temperature control of the microflow reactor. Room temperature is understood by the artisan, but typically includes those temperatures that are typical for a laboratory or production plant facility, such as 20° C. to 25° C.

The product stream that exits from an exit port of the microflow reactor will typically have a polar portion and an organic portion. Because the polar liquid and the organic liquid are immiscible, the organic and polar liquids can separate into two phases in the product stream. However, in practice when the product is a benzophenonyl (alk)acrylic ester or substituted benzophenonyl (alk)acrylic ester, the two phases are typically poorly-defined and without a well-defined phase boundary. This is particularly the case when typical solvents, such as ethyl acetate, are used as the organic liquid. This can cause two problems. First, the reaction byproducts, such as (alk)acrylic acid, which can be formed, for example, by the reaction of excess (alk)acryloyl halide or 3-haloalkylcarboxyl halide with water when water is the polar liquid, can be present in both the polar and the organic portions. Second, it can be difficult to separate the organic and polar phases under such circumstances (i.e., when the phase boundary between the phases is not distinct), thereby causing loss of product and a less efficient process.

These problems can be solved conveniently by use of an (alk)acrylic ester compound of Formula (I). In the compound of Formula (I), $R_1$ is alkyl or H and $R_2$ is C1 to C12 alkyl, optionally interrupted by one or more O atoms, and most commonly interrupted by either 0 or 1 O atoms.

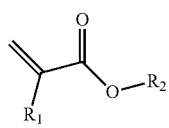

Formula (I)

In the compound of Formula (I), $R_1$ is often H or C1 to C4 alkyl, such as H or C1 to C2 alkyl, or even H or methyl. $R_2$ is often C1-C12 alkyl, such as C4-C12 alkyl, or the $C_4H_3O$ (i.e., tetrahydrofuranyl) radical.

The compound of Formula (I) is a (alk)acrylic ester. Surprisingly, the (alk)acrylic esters that are most effective at promoting phase separation are those with a relatively short $R_2$, specifically, those wherein $R_2$ is C1 to C12 alkyl, optionally interrupted by one or more O atoms. Longer chain $R_2$ moieties are less effective. For example, when $R_2$ is C18, it is less effective at promoting a sharp phase boundary than when $R_2$ is n-butyl (i.e., C4).

This result is surprising and unexpected. A person of skill in the art understands that longer chain alkyl groups are more hydrophobic than shorter chained alkyl groups, and thus would expect that (alk)acrylic esters with longer chain alkyl ester groups would be more effective at inducing clean phase separation and a sharp phase boundary because they would be more effective at increasing the hydrophobicity of the organic liquid, thereby differentiating it from the polar liquid. Unexpectedly and surprisingly, this is not the case. When (alk)acrylic esters having alkyl esters of more than C12 are used, they actually prove less effective for this purpose than groups that are C12 or less, i.e., than compounds of Formula (I).

Particular examples of compounds of Formula (I) include methyl methacrylate, butyl acrylate, tetrahydrofuranyl acrylate, 2-ethyl hexyl acrylate, and 2-methyl heptyl acrylate. Other compounds of Formula (I) can also be used.

The compound of Formula (I) can be used various ways to solve the phase separation problem discussed above. In a first example, it is possible to use the compound of Formula (I) or (II) as the polar liquid. In this case, the compound of Formula (I) is used to dissolve the benzophenone alcohol or substituted benzophenone alcohol starting material. The solution of benzophenone alcohol or substituted benzophenone alcohol starting material in the compound of Formula (I) is then added to the mixing chamber of the microflow reactor as described herein.

When the compound of Formula (I) is used as the organic liquid to disperse the benzophenone alcohol or substituted benzophenone alcohol, the concentration of the benzophenone alcohol or substituted benzophenone alcohol in the compound of Formula (I) will vary depending on the solubility of the benzophenone alcohol or substituted benzophenone alcohol in the compound of Formula (I). In most cases, benzophenone alcohol or substituted benzophenone alcohol will be dissolved in the compound of Formula (I), so the concentration can be any concentration in which the benzophenone alcohol or substituted benzophenone alcohol forms a solution in the compound of Formula (I). Typical concentrations are from 0.01% by weight to 30% by weight of the benzophenone alcohol or substituted benzophenone alcohol. The concentration can be adjusted as necessary, within the solubility limits, in order to be able to achieve an appropriate molar flow ratio of the benzophenone alcohol or substituted benzophenone alcohol to the other starting materials as described herein.

Water can be added to the product stream to help remove any byproducts from the organic liquid. This can be done in any suitable manner. For example, the product stream can exit the mixing chamber of the microflow reactor and travel into tubing, which can then connect with additional tubing through which water is pumped by way of a Y or T connector.

The organic and polar phases, the latter of which can be an aqueous phase, particularly when a water wash is used, can be separated, for example, with known apparatuses that are useful for separating different phases in a flow process. Such an apparatus can function by providing a membrane that is wettable by only one of the organic phase and the polar phase, the latter of which can be an aqueous phase. The apparatus can provide a pressure differential across the membrane such that only the phase that wets the membrane can pass through the membrane. In a typical apparatus, the membrane is hydrophobic and permits the organic phase to pass through.

Thus, the apparatus can function by providing an inlet port for the product stream, which has a combination of an organic phase and a polar phase, the latter of which can be an aqueous phase. The apparatus can also have two outlet ports, each of which is in communication with opposite sides of a membrane as described herein. In use, a product stream with two phases, an organic phase and a polar phase, can enter the apparatus by way of the inlet port. One of the two phases, typically the organic phase, passes through the membrane and subsequently exits the apparatus by way of a first outlet port. The other phase, typically the polar phase, which can be an aqueous phase, does not pass through the membrane and subsequently exits the apparatus by way of a second outlet port.

Apparatuses for separating organic and polar phases as described herein are commercially available, for example, under the trade designations SEP-10, SEP-200-SS, and SEP-200-HS from Zaiput Flow Technologies, Cambridge, Mass., USA.

In a second example of using the compound of Formula (I), it is possible to add the compound to the product stream in a batch processing step. In this example, the product stream is collected in a vessel to which is added the compound of Formula (I), and optionally water. The amount of the compound of Formula (I) that is added should be sufficient to dissolve the collected benzophenonyl (alk)

acrylic ester or substituted benzophenonyl (alk)acrylic ester reaction product. In the batch process, the organic portion, which contains the organic liquid, such as ethyl acetate, the benzophenonyl (alk)acrylic ester or substituted benzophenonyl (alk)acrylic ester and compound of Formula (I) is then separated from the polar liquid, which typically contains salts, byproducts, and water. This can be accomplished by means known in the art, such as a separatory funnel or Dean Stark trap. If desired, any volatile organic liquid, such as ethyl acetate, can then be removed, for example, by evaporation.

The use of the compounds of Formulas (I) as described herein can, in many cases, offer one or more useful advantages. First, as discussed above, it can effect good phase separation and a sharp phase boundary between the organic and polar phases thus facilitating separation of the two phases and recovery of the product from the organic phase. This clean separation also removes byproducts and salts from the organic liquid, and therefore can provide a mixture of benzophenonyl (alk)acrylic ester or substituted benzophenonyl (alk)acrylic ester and compound of Formula (I) that is ready for use in subsequent processes. For example, because the compounds of Formula (I) have acrylate moieties, they can be subsequently co-polymerized with the benzophenonyl (alk)acrylic ester or substituted benzophenonyl (alk)acrylic ester that is formed in the mixing chamber of the microflow reactor. Thus, it is possible for the product stream of the process described herein to be fed directly into another reactor, such as a microflow reactor, for subsequent polymerization. When the compound of Formula (I) is used as the organic liquid and the polar liquid is removed in a continuous process in-line as described herein, the presently described reaction and subsequent polymerization of the benzophenonyl (alk)acrylic ester or substituted benzophenonyl (alk)acrylic ester and compound of Formula (I) can be performed as a continuous process.

Thus, the process described herein is considered to be industrially acceptable when the product stream contains benzophenonyl (alk)acrylic ester or substituted benzophenonyl (alk)acrylic ester in an amount of no less than 80 wt % based on the total weight of benzophenonyl (alk)acrylic ester or substituted benzophenonyl (alk)acrylic ester, unreacted starting material, and organic byproducts in the product stream, but not including the weight of any compound of Formula (I) in the product stream. Lower yields are not suitable for industrial purposes and are considered unacceptable. In many cases, the yield is even higher, though this is not required. In some cases, the amount of benzophenonyl (alk)acrylic ester or substituted benzophenonyl (alk)acrylic ester is 85 wt % or greater, 90 wt % or greater, or even 95 wt % or greater, in each case based on the total weight benzophenonyl (alk)acrylic ester or substituted benzophenonyl (alk)acrylic ester, unreacted starting material, and organic byproducts in the product stream, but not including the weight of any compound of Formula (I) in the product stream. The weights of these components of the product stream can be measured by any suitable means, for example, by gas chromatography. When gas chromatography is used, the compounds in the product stream can be identified by comparing their retention time to that of standards on the same column. The areas for the peaks can be calculated using standard software, or even manually, and then converted into concentration by using calibration curves. The calibration curves can be established by standard samples having known concentrations of the compounds. Other suitable means of determining the wt % of the various components of the product stream include liquid chromatography, such as HPLC, and gas chromatography, such as GC/MS.

That such high yields of benzophenonyl (alk)acrylic ester or substituted benzophenonyl (alk)acrylic ester can be obtained under the reaction conditions discussed herein is surprising. (Alk)acryloyl halides and 3-haloalkylcarboxyl halides are well known to be highly reactive with polar liquids, such as water, to provide corresponding acids. Despite the expectation that the presence of a polar liquid like water would rapidly hydrolyze the (alk)acryloyl halide or 3-haloalkylcarboxyl halide, the process described herein uses a polar liquid, typically water, yet surprisingly hydrolysis is not the major reaction and high yields of product can be achieved. Further, the reaction between (alk)acryloyl halide or 3-haloalkylcarboxyl halide is known to be highly exothermic, thus requiring external cooling to avoid dangerous release of heat, unwanted side reactions, or both. Surprisingly, the method disclosed herein proceed in high yields even when performed at room temperature and without the use of a cooling device for the microflow reactor.

LIST OF ILLUSTRATIVE EMBODIMENTS

The following list illustrates particular embodiments of the present disclosure, but is not intended to be limiting. Other embodiments, not illustrated here, are also contemplated.

1. A method of making a benzophenonyl (alk)acrylic ester or substituted benzophenonyl (alk)acrylic ester comprising
   adding to a mixing chamber of a microflow reactor
   a benzophenone alcohol or substituted benzophenone alcohol comprising at least one hydroxy moiety,
   one or more bases that are sufficient to at least partially deprotonate the benzophenone alcohol or substituted benzophenone alcohol,
   a polar liquid,
   an (alk)acryloyl halide or 3-haloalkylcarboxyl halide, and
   an organic liquid that is immiscible with the polar liquid in a sufficient amount to dissolve the (alk)acryloyl halide or 3-haloalkylcarboxyl halide, wherein
   the molar flow ratio of all of the hydroxy moieties to the sum of all of the one or more bases is 1 to at least 1.1; and
   producing a product stream comprising one or more benzophenonyl (alk)acrylic ester or substituted benzophenonyl (alk)acrylic ester and one or more salts of the one or more bases; and wherein
   the polar liquid added to the mixing chamber is sufficient to dissolve the one or more salts; and
   the product stream has an organic portion and a polar portion, the organic portion of the product stream comprising the benzophenonyl (alk)acrylic ester or substituted benzophenonyl (alk)acrylic ester in an amount of at least 80 wt % based on the total weight of the benzophenonyl (alk)acrylic ester or substituted benzophenonyl (alk)acrylic ester, unreacted benzophenone alcohol or substituted benzophenone alcohol, and organic byproducts in the product stream; and further wherein either
   (a) the organic liquid comprises a compound of Formula (I); or
   (b) the method further comprises adding a compound of Formula (I) to the product stream; or
   (c) the organic liquid comprises a compound of Formula (I) and the method further comprises adding a compound of Formula (I) to the product stream

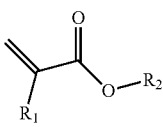

Formula (I)

wherein
R$_1$ is H or C1 to C4 alkyl; and
R$_2$ is C1 to C12 alkyl optionally interrupted by one or more O atoms.

2. A method of making a benzophenonyl (alk)acrylic ester or substituted benzophenonyl (alk)acrylic ester comprising
adding to a mixing chamber of a microflow reactor,
a benzophenone alcohol or substituted benzophenone alcohol comprising at least one hydroxy moiety,
one or more bases that are sufficient to at least partially deprotonate the benzophenone alcohol or substituted benzophenone alcohol,
a polar liquid,
an (alk)acryloyl halide or 3-haloalkylcarboxyl halide, and
an organic liquid that is immiscible with the polar liquid in a sufficient amount to dissolve the (alk)acryloyl halide or 3-haloalkylcarboxyl halide, wherein
the molar flow ratio of all of the hydroxy moieties to the sum of all of the one or more bases is 1 to at least 1.1; and
producing a product stream comprising one or more benzophenonyl (alk)acrylic ester or substituted benzophenonyl (alk)acrylic ester and one or more salts of the one or more bases; and wherein
the polar liquid added to the mixing chamber is sufficient to dissolve the one or more salts; and
the product stream has an organic portion and a polar portion, the organic portion of the product stream comprising the benzophenonyl (alk)acrylic ester or substituted benzophenonyl (alk)acrylic ester in an amount of at least 80 wt % based on the total weight of the benzophenonyl (alk)acrylic ester or substituted benzophenonyl (alk)acrylic ester, unreacted benzophenone alcohol or substituted benzophenone alcohol, and organic byproducts in the product stream;
the process characterized in that either:
(a) the organic liquid comprises a compound of Formula (I); or
(b) the method further comprises adding a compound of Formula (I) to the product stream; or
(c) the organic liquid comprises a compound of Formula (I) and the method further comprises adding a compound of Formula (to the product stream

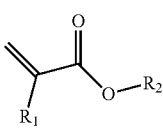

Formula (I)

wherein
R$_1$ is H or C1 to C4 alkyl; and
R$_2$ is C1 to C12 alkyl optionally interrupted by one or more O atoms.

3. The method of any of the preceding embodiments, wherein the organic liquid comprises a compound of Formula (I).

4. The method of any of the preceding embodiments, wherein the method further comprises adding a compound of Formula (I) to the product stream.

5. The method of any of the preceding embodiments, wherein the amount of the benzophenonyl (alk)acrylic ester or substituted benzophenonyl (alk)acrylic ester in the product stream is at least 85 wt % based on the total weight of the benzophenonyl (alk)acrylic ester or substituted benzophenonyl (alk)acrylic ester, unreacted benzophenone alcohol or substituted benzophenone alcohol, and organic byproducts in the product stream.

6. The method of any of the preceding embodiments, wherein the amount of the benzophenonyl (alk)acrylic ester or substituted benzophenonyl (alk)acrylic ester in the product stream is least 90 wt % based on the total weight of the benzophenonyl (alk)acrylic ester or substituted benzophenonyl (alk)acrylic ester, unreacted benzophenone alcohol or substituted benzophenone alcohol, and organic byproducts in the product stream.

7. The method of any of the preceding embodiments, wherein the amount of the benzophenonyl (alk)acrylic ester or substituted benzophenonyl (alk)acrylic ester in the product stream is at least 95 wt % based on the total weight of the benzophenonyl (alk)acrylic ester or substituted benzophenonyl (alk)acrylic ester, unreacted benzophenone alcohol or substituted benzophenone alcohol, and organic byproducts in the product stream.

8. The method of any of the preceding embodiments, wherein the polar liquid comprises water, methanol, ethanol, propanol, or a mixture thereof.

9. The method of any of the preceding embodiments, wherein the polar liquid comprises water.

10. The method of any of the preceding embodiments, wherein the polar liquid is water.

11. The method of embodiment 10, wherein the water is deionized water, distilled water, or reverse osmosis water.

12. The method of the preceding embodiments, wherein the benzophenone alcohol or substituted benzophenone alcohol is a monoalcohol having only one hydroxy radical.

13. The method of any of embodiments 1-11, wherein the benzophenone alcohol or substituted benzophenone alcohol is a poly alcohol having more than one hydroxy radical.

14. The method of the preceding embodiments, wherein the benzophenone alcohol or substituted benzophenone alcohol is 4-hydroxy benzophenone, 4-hydroxyethyl benzophenone, 2-hydroxybenzophenone, 3-hydroxybenzophenone, 4-chloro 4'-hydroxy benzophenone, 5-bromo 2-hydroxybenzophenone, 5-chloro 2-hydroxybenzophenone, and the like.

15. The method of the preceding embodiments, wherein the benzophenone alcohol is 4-hydroxy benzophenone.

16. The method of any of the preceding embodiments, wherein the one or more bases comprises at least one of triethyl amine, dimethyl amine, trimethyl amine, methyldiethyl amine, alkali metal hydroxide, and alkali earth metal hydroxide.

17. The method of any of the preceding embodiments, wherein the one or more bases comprises triethyl amine.

18. The method of any of the preceding embodiments, wherein the one or more bases comprises potassium hydroxide, sodium hydroxide, or a mixture thereof.

19. The method of any of the preceding embodiments, further comprising a step of adding water to the product stream.

20. The method of embodiment 19 wherein the water is added to the product stream in a continuous manner after the product stream exits an exit port of the mixing chamber of the microflow reactor.

21. The method of any of embodiments 19-20, wherein the water that is added to the product stream is distilled water, deionized water, or reverse osmosis water.

22. The method of any of embodiments 19-21, wherein the polar portion is continuously separated from the organic portion of the product stream.

23. The method of embodiment 22, wherein the step of continuously separating the polar portion comprises passing the product stream through an apparatus comprising a membrane wettable by only one of the polar phase or the organic phase, and a pressure difference across the membrane such that only one of polar portion or the organic portion passes through the membrane, thereby separating the polar portion from the organic portion of the product stream.

24. The method of any of the preceding embodiments, wherein the step of adding the benzophenone alcohol or substituted benzophenone alcohol to the mixing chamber of the microflow reactor comprises adding a second alcohol to the mixing chamber of the microflow reactor.

25. The method of any of embodiments 1-24, wherein the step of adding the benzophenone alcohol or substituted benzophenone alcohol to the mixing chamber of the microflow reactor comprises adding only one type benzophenone alcohol or substituted benzophenone alcohol and no other alcohols to the mixing chamber of the microflow reactor.

26. The method of any of the preceding embodiments, wherein the step of adding the benzophenone alcohol or substituted benzophenone alcohol to the mixing chamber of the microflow reactor comprises adding a solution of benzophenone alcohol or substituted benzophenone alcohol in the organic liquid to the mixing chamber of the microflow reactor.

27. The method of any of the preceding embodiments, wherein the organic liquid comprises one or more of dichloromethane, ethyl acetate, butyl acetate, methyl ethyl ketone, methyl butyl ketone, or one or more compounds of Formula (I).

28. The method of embodiment 27, wherein the organic liquid comprises one or more compounds of Formula (I).

29. The method of embodiment 27, wherein the organic liquid is one or more compounds of Formula (I).

30. The method of any of the preceding embodiments, wherein in the compound of Formula (I), $R_2$ is C1-C12 alkyl.

31. The method of any of the preceding embodiments, wherein $R_1$ is methyl or H.

32. The method of embodiment 31, wherein $R_1$ is methyl.

33. The method of embodiment 31, wherein $R_1$ is H.

34. The method of any of the preceding embodiments, wherein $R_2$ is C1.

35. The method of any embodiments 1-33, wherein $R_2$ is C2.

36. The method of any embodiments 1-33, wherein $R_2$ is C3.

37. The method of any embodiments 1-33, wherein $R_2$ is C4.

38. The method of any embodiments 1-33, wherein $R_2$ is C5.

39. The method of any embodiments 1-33, wherein $R_2$ is C6.

40. The method of any embodiments 1-33, wherein $R_2$ is C7.

41. The method of any embodiments 1-33, wherein $R_2$ is C8.

42. The method of any embodiments 1-33, wherein $R_2$ is C9.

43. The method of any embodiments 1-33, wherein $R_2$ is C10.

44. The method of any embodiments 1-33, wherein $R_2$ is C11.

45. The method of any embodiments 1-33, wherein $R_2$ is C12.

46. The method of any of embodiments 1-33, wherein $R_2$ is 2-ethyl hexyl.

47. The method of any of embodiments 1-33, wherein $R_2$ is 2-methyl heptyl.

48. The method of any of the preceding embodiments, wherein the (alk)acryloyl halide or 3-haloalkylcarboxyl halide is an (alk)acryloyl halide.

49. The method of embodiment 48, wherein the (alk)acryloyl halide comprises an alkyl group that is C10 or less.

50. The method of embodiment 48, wherein the (alk)acryloyl halide comprises an alkyl group that is C9 or less.

51. The method of embodiment 48, wherein the (alk)acryloyl halide comprises an alkyl group that is C8 or less.

52. The method of embodiment 48, wherein the (alk)acryloyl halide comprises an alkyl group that is C7 or less.

53. The method of embodiment 48, wherein the (alk)acryloyl halide comprises an alkyl group that is C6 or less.

54. The method of embodiment 48, wherein the (alk)acryloyl halide comprises an alkyl group that is C5 or less.

55. The method of embodiment 48, wherein the (alk)acryloyl halide comprises an alkyl group that is C4 or less.

56. The method of embodiment 48, wherein the (alk)acryloyl halide comprises an alkyl group that is C3 or less.

57. The method of embodiment 48, wherein the (alk)acryloyl halide comprises an alkyl group that is C2 or less.

58. The method of embodiment 48, wherein the (alk)acryloyl halide is acryloyl halide or methacryloyl halide.

59. The method of any of embodiments 48-58, wherein the halide of the (alk)acryloyl halide is chloride.

60. The method of any of the preceding embodiments, wherein the (alk)acryloyl halide is acryloyl chloride or methacryloyl chloride.

61. The method of any of the preceding embodiments, wherein the (alk)acryloyl halide is acryloyl chloride.

62. The method of any of embodiments 1-60, wherein the (alk)acryloyl halide is methacryloyl chloride.

63. The method of any of embodiments 1-47, wherein the (alk)acryloyl halide or 3-haloalkylcarboxyl halide is 3-haloalkylcarboxyl halide.

64. The method of embodiment 63, wherein the halo group of the 3-haloalkylcarboxyl halide is chloro.

65. The method of embodiment 63 or 64, wherein the haloalkyl group is C30 or less.

66. The method of embodiment 63 or 64, wherein the haloalkyl group is C25 or less.

67. The method of embodiment 63 or 64, wherein the haloalkyl group is C24 or less.

68. The method of embodiment 63 or 64, wherein the haloalkyl group is C22 or less.

69. The method of embodiment 63 or 64, wherein the haloalkyl group is C20 or less.

70. The method of embodiment 63 or 64, wherein the haloalkyl group is C18 or less.

71. The method of embodiment 63 or 64, wherein the haloalkyl group is C16 or less.

72. The method of embodiment 63 or 64, wherein the haloalkyl group is C12 or less.

73. The method of embodiment 63 or 64, wherein the haloalkyl group is C10 or less.
74. The method of embodiment 63 or 64, wherein the haloalkyl group is C8 or less.
75. The method of embodiment 63 or 64, wherein the haloalkyl group is C7 or less.
76. The method of embodiment 63 or 64, wherein the haloalkyl group is C6 or less.
77. The method of embodiment 63 or 64, wherein the haloalkyl group is C5 or less.
78. The method of embodiment 63 or 64, wherein the haloalkyl group is C4 or less.
79. The method of embodiment 63 or 64, wherein the haloalkyl group is C3 or less.
80. The method of any of the preceding embodiments, wherein the halide of the 3-haloalkyl carboxyl halide is chloride.
81. The method of any of the preceding embodiments, wherein the 3-haloalkyl carboxyl halide is 3-chloropropionyl chloride.
82. The method of any of the preceding embodiments, wherein the step of adding the benzophenone alcohol or substituted benzophenone alcohol to the mixing chamber of the microflow reactor comprises adding a mixture of the benzophenone alcohol or substituted benzophenone alcohol and at least one of the one or more bases to the mixing chamber of the microflow reactor.
83. The method of embodiment 82, wherein the mixture of the benzophenone alcohol or substituted benzophenone alcohol and at least one of the one or more bases is added as a solution in the polar liquid.
84. The method of any of the preceding embodiments, wherein the step of adding the benzophenone alcohol or substituted benzophenone alcohol to the mixing chamber of the microflow reactor comprises adding the benzophenone alcohol or substituted benzophenone alcohol to the mixing chamber of the microflow reactor through a first addition port.
85. The method of any of the preceding embodiments, wherein the step of adding the (alk)acryloyl halide or a 3-haloalkylcarboxyl halide to the mixing chamber of the microflow reactor comprises adding the (alk)acryloyl halide or a 3-haloalkylcarboxyl halide to the mixing chamber of the microflow reactor through a second addition port.
86. The method of any of the preceding embodiments, wherein the step of adding the benzophenone alcohol or substituted benzophenone alcohol to the mixing chamber of the microflow reactor comprises adding a mixture of the benzophenone alcohol or substituted benzophenone alcohol, the polar liquid, and the one or more bases to the mixing chamber of the microflow reactor through a first addition port.
87. The method of any of the preceding embodiments, wherein the step of adding the (alk)acryloyl halide or a 3-haloalkylcarboxyl halide to the mixing chamber of the microflow reactor comprises adding a solution of the (alk)acryloyl halide or a 3-haloalkylcarboxyl halide in the organic liquid to the mixing chamber of the microflow reactor through a second addition port.
88. The method of any of the preceding embodiments, wherein the molar flow ratio of the benzophenone alcohol or substituted benzophenone alcohol to the (alk)acryloyl halide or 3-haloalkylcarboxyl halide is 1 to at least 1.1.
89. The method of any of the preceding embodiments, wherein the molar flow ratio of the benzophenone alcohol or substituted benzophenone alcohol to the (alk)acryloyl halide or 3-haloalkylcarboxyl halide is 1 to at least 1.2.
90. The method of any of the preceding embodiments, wherein the molar flow ratio of the benzophenone alcohol or substituted benzophenone alcohol to the (alk)acryloyl halide or 3-haloalkylcarboxyl halide is 1 to at least 1.3.
91. The method of any of the preceding embodiments, wherein the molar flow ratio of the benzophenone alcohol or substituted benzophenone alcohol to the (alk)acryloyl halide or 3-haloalkylcarboxyl halide is 1 to at least 1.4.
92. The method of any of the preceding embodiments, wherein the molar flow ratio of the benzophenone alcohol or substituted benzophenone alcohol to the (alk)acryloyl halide or 3-haloalkylcarboxyl halide is 1 to at least 1.5.
93. The method of any of the preceding embodiments, wherein the molar flow ratio of the benzophenone alcohol or substituted benzophenone alcohol to the (alk)acryloyl halide or 3-haloalkylcarboxyl halide is 1 to at least 1.6.
94. The method of any of the preceding embodiments, wherein the molar flow ratio of the benzophenone alcohol or substituted benzophenone alcohol to the (alk)acryloyl halide or 3-haloalkylcarboxyl halide is 1 to at least 1.7.
95. The method of any of the preceding embodiments, wherein the molar flow ratio of the benzophenone alcohol or substituted benzophenone alcohol to the (alk)acryloyl halide or 3-haloalkylcarboxyl halide is 1 to at least 1.8.
96. The method of any of the preceding embodiments, wherein the molar flow ratio of the benzophenone alcohol or substituted benzophenone alcohol to the (alk)acryloyl halide or 3-haloalkylcarboxyl halide is 1 to at least 1.9.
97. The method of any of the preceding embodiments, wherein the molar flow ratio of the benzophenone alcohol or substituted benzophenone alcohol to the (alk)acryloyl halide or 3-haloalkylcarboxyl halide is 1 to at least 2.0.
98. The method of any of the preceding embodiments, wherein the molar flow ratio of the benzophenone alcohol or substituted benzophenone alcohol to the (alk)acryloyl halide or 3-haloalkylcarboxyl halide is 1 to at least 2.1.
99 The method of any of the preceding embodiments, wherein the molar flow ratio of the benzophenone alcohol or substituted benzophenone alcohol to the (alk)acryloyl halide or 3-haloalkylcarboxyl halide is 1 to at least 2.2.
100. The method of any of the preceding embodiments, wherein the molar flow ratio of the benzophenone alcohol or substituted benzophenone alcohol to the (alk)acryloyl halide or 3-haloalkylcarboxyl halide is 1 to at least 2.3.
101. The method of any of the preceding embodiments, wherein the molar flow ratio of the benzophenone alcohol or substituted benzophenone alcohol to the (alk)acryloyl halide or 3-haloalkylcarboxyl halide is 1 to at least 2.4.
102. The method of any of the preceding embodiments, wherein the molar flow ratio of the benzophenone alcohol or substituted benzophenone alcohol to the (alk)acryloyl halide or 3-haloalkylcarboxyl halide is 1 to at least 2.5.
103. The method of any of the preceding embodiments, wherein the molar flow ratio of the benzophenone alcohol or substituted benzophenone alcohol to the sum of all of the at least one bases is 1 to at least 1.5
104. The method of any of the preceding embodiments, wherein the molar flow ratio of the benzophenone alcohol or substituted benzophenone alcohol to the sum of all of the at least one bases is 1 to at least 1.8.
105. The method of any of the preceding embodiments, wherein the molar flow ratio of the benzophenone alcohol or substituted benzophenone alcohol to the sum of all of the at least one bases is 1 to at least 1.9.
106. The method of any of the preceding embodiments, wherein the molar flow ratio of the benzophenone alcohol or substituted benzophenone alcohol to the sum of all of the at least one bases is 1 to at least 2.0.

107. The method of any of the preceding embodiments, wherein the molar flow ratio of the benzophenone alcohol or substituted benzophenone alcohol to the sum of all of the at least one bases is 1 to at least 2.1.

108. The method of any of the preceding embodiments, wherein the molar flow ratio of the benzophenone alcohol or substituted benzophenone alcohol to the sum of all of the at least one bases is 1 to at least 2.2.

109. The method of any of the preceding embodiments, wherein the molar flow ratio of the benzophenone alcohol or substituted benzophenone alcohol to the sum of all of the at least one bases is 1 to at least 2.3.

110. The method of any of the preceding embodiments, wherein the molar flow ratio of the benzophenone alcohol or substituted benzophenone alcohol to the sum of all of the at least one bases is 1 to at least 2.4.

111. The method of any of the preceding embodiments, wherein the molar flow ratio of the benzophenone alcohol or substituted benzophenone alcohol to the sum of all of the at least one bases is 1 to at least 2.5.

112. The method of any of the preceding embodiments, wherein the microflow reactor is not temperature controlled during the method.

113. The method of any of the preceding embodiments, wherein the mixing chamber of the microflow reactor has an internal volume of no more than 5 mL.

114. The method of any of the preceding embodiments, wherein the mixing chamber of the microflow reactor has an internal volume of no more than 1 mL.

115. The method of any of the preceding embodiments, wherein the mixing chamber of the microflow reactor has an internal volume of no more than 800 µL.

116. The method of any of the preceding embodiments, wherein the mixing chamber of the microflow reactor has an internal volume of no more than 750 µL.

117. The method of any of the preceding embodiments, wherein the mixing chamber of the microflow reactor has an internal volume of no more than 600 µL.

118. The method of any of the preceding embodiments, wherein the mixing chamber of the microflow reactor has an internal volume of no more than 500 µL.

119. The method of any of the preceding embodiments, wherein the mixing chamber of the microflow reactor has an internal volume of no more than 400 µL.

120. The method of any of the preceding embodiments, wherein the mixing chamber of the microflow reactor has an internal volume of no more than 300 µL.

121. The method of any of the preceding embodiments, wherein the mixing chamber of the microflow reactor has an internal volume of no more than 250 µL.

122. The method of any of the preceding embodiments, wherein the mixing chamber of the microflow reactor has an internal volume of no more than 200 µL.

123. The method of any of the preceding embodiments, wherein the mixing chamber of the microflow reactor has an internal volume of no more than 100 µL.

124. The method of any of the preceding embodiments, wherein the mixing chamber of the microflow reactor has an internal volume of no more than 50 µL.

125. The method of any of the preceding embodiments, wherein the method further comprises a rinsing step that occurs before the adding step, the rinsing step comprising flowing a rinsing solvent through the mixing chamber of the microflow reactor and out of an exit port.

126. The method of embodiment 125, wherein the rinsing solvent comprises water, ethanol, propanol, or a mixture thereof.

127. The method of embodiment 126, wherein the rinsing solvent is water.

128. The method of embodiment 125, wherein the rinsing solvent is selected to be the same as the polar liquid.

129. The method of any of the preceding embodiments, wherein the method further comprises a priming step that occurs before the adding step, the priming step comprising flowing the alcohol through the mixing chamber of the microflow reactor and out of an exit port.

130. The method of embodiment 129, wherein the priming step consists of flowing a solution of the benzophenone alcohol or substituted benzophenone alcohol through the mixing chamber of the microflow reactor and out of an exit port.

131. The method of any of embodiments 129-130, wherein the priming step takes place after a rinsing step.

132. The method of embodiment 131, wherein the rinsing step is the rinsing step of any of embodiments 125-128.

133. The method of any of the preceding embodiments, wherein the microflow reactor is an impinging flow reactor.

134. The method of any of the preceding embodiments, wherein the microflow reactor is not cooled by cooling equipment.

135. The method of any of the preceding embodiments, wherein the mixing chamber of the microflow reactor is not cooled by cooling equipment.

136. The method of any of the preceding embodiments, wherein the method is carried out at room temperature.

137. The method of any of the preceding embodiments, wherein
the mixing chamber of the microflow reactor comprises an exit port; and
wherein the method further comprises a step of removing the (alk)acrylic ester from the exit port simultaneously with the adding step.

EXAMPLES

All materials are commercially available, for example from Sigma-Aldrich Chemical Company, Milwaukee, Wis., USA, or known to those skilled in the art, unless otherwise stated or apparent.

The following abbreviations are used in this section: NMR=nuclear magnetic resonance, MHz=megahertz, mL=milliliters, µL=microliters, sec=seconds, min=minutes, g=grams, µm=micrometers, mm=millimeters, cm=centimeters, m=meters, ppm=parts per million, mol=moles, mol %=mole percent. Abbreviations of materials used in this section, as well as descriptions of the materials, are provided in Table A.

Materials

Table A

| Material | Details |
|---|---|
| BP | 4-hydroxybenzophenone, available from Aldrich, Belgium |
| ACl | Acryloylchloride, available from ABCR, Germany |
| 3CPC | 3-chloropropionylchloride, available from Aldrich, Belgium |
| TEA | Triethylamine, available from Aldrich, Belgium |
| EtOAc | Ethylacetate, available from Aldrich, Belgium |
| Water | De-ionized water |
| NaOH | Sodium hydroxide, available from Aldrich, Belgium |
| IOA | Isooctyl acrylate, available from Aldrich, Belgium |
| 2 EHA | 2-Ethylhexyl acrylate, available from Aldrich, Belgium |

Table A-continued

| Material | Details |
|---|---|
| BA | Butyl acrylate, available from Aldrich, Belgium |
| BMA | Butyl methacrylate, available from Aldrich, Belgium |
| PHA | 2-propylheptyl acrylate, available from BASF, Ludwigshafen, Germany |
| 2 OA | Octyl acrylate, available from Aldrich, Belgium |
| 2 EHMA | 2-Ethylhexyl methacrylate, available from Aldrich, Belgium |
| THFA | Tetrahydrofurfuryl acrylate, available from Aldrich, Belgium |
| LMA | Lauryl methacrylate, available from Aldrich, Belgium |
| C18 | Octadecyl acrylate, available from Aldrich, Belgium |
| PFA tubing | Perfluoroalkoxy tubing, available from ACHROM, Belgium |

Microreactor Description

Reactions for examples described below were performed using amicroreactor having a mixing device having five addition ports with an internal volume of approximately 23 µL available under the trade designation "IDEX 91" from ACHROM, Belgium. HPLC pumps, available under the trade designation Chemyx Fusion 100 Touch from KR Analytical, Cheshire, UK, delivered at least two reactant streams from at least two containers through PFA tubing with an inner diameter of 0.5 mm, available under the trade designation "IDEX 1512L" from ACHROM, to at least two addition ports of the mixing device using connectors available from ACHROM. The at least two reactant streams combined within the internal volume of the mixing device where a product stream was formed. The product stream exited the mixing device through a product port and flowed through PFA tubing with an inner diameter of 1 cm, available under from ACHROM, cut to a length of 10 cm, connected to the product port using connectors available from ACHROM, and then into a PFA tubing with an inner diameter of 0.7 mm, available from ACHROM, cut to a length of 150 cm, connected to the 1 cm diameter tubing using connectors available from ACHROM, into a collection vessel.

Molar Ratio

The term "Molar Ratio" is used throughout this section to mean the ratio or ratios of moles of indicated reactants added to a vessel used to contain a batch reaction. For example, if 1 mole of Component C and 2 moles of Component D are added to a reaction vessel, the molar ratio of Component C to Component D is 1:2.

% Composition

The term "% Composition" is used throughout this section to mean the percent, by weight, of the specified compound in the organic portion of the product stream, with respect to the combination of all components identified in the organic portion of the product stream by gas chromatography (GC), excluding solvent. The concentrations were determined by GC, as described below, under "Characterization." Samples were collected from the organic layer in the collection vessel receiving the product stream during experiments. After initiating flow in an experiment, the first five or more reactor volumes of product stream were discarded and not included in the volume sampled for analysis.

Characterization

GC

The concentration of solutes in the product stream from the microreactor in experiments was determined using a gas chromatograph (GC) available under the trade designation "6890N" from Agilent Technologies, USA, using a flame ionization detector. The column used was a 95% polydimethylsiloxane/5% polydiphenylsiloxane, 30 m length, 0.32 mm diameter, 0.25 µm film thickness, available under the trade designation "HP-5" from Agilent Technologies, USA. Hydrogen was used as the carrier gas. Areas of peaks for compounds identified by retention time were converted to concentration values using calibration curves established for known concentrations of standards of the compounds.

NMR

Analysis by NMR was made using a Bruker Avance 300 Digital NMR spectrometer equipped with Bruker 5 mm BBFO 300 MHz Z-gradient high resolution-ATM probe. The samples were placed in NMR tubes available under the trade designation "WG-5M-ECONOMY" from Aldrich, Belgium. TMS (tetramethylsilane, available from Aldrich, Belgium) was added as a zero ppm reference. Proton NMR spectra were acquired using the following parameters:

Pulse Angle: 30°
Number of Scans: 128
Acquisition Time: 5.3 sec
Relaxation time: 2.0 sec Except where noted, NMR confirmed the identity of the desired products.

Examples 1 Through 4 (EX-1 Through EX-4)

For EX-1, the following procedure was carried out using the microreactor described above, with the mixing device at ambient temperature. Container I contained 100 g BP, 50 g TEA, 20 G NaOH, and 147 g water. Container II contained 40 g ACl and 80 g EtOAc. Each container was connected to a pump and the pump speeds were controlled to deliver the mixtures in the containers at the following rates: Container I; 14 mL/min, or 0.022 mol/min of BP; Container II: 7 mL/min, or 0.028 mol/min of ACl. The two unused addition ports of the mixing device were sealed with plugs. The molar flow ratios of BP:NaOH:TEA:ACl pumped to the mixing device were approximately 1:1:1:1.24. Separation of aqueous phase and an organic phase was observed in the collection vessel. The organic phase was observed to have a hazy appearance. The aqueous layer was removed from the collection vessel. Results of analysis of the organic layer by GC and NMR are presented in Table 1.

15 g IOA was added to 30 g of the product stream from the reactor, with the resulting aqueous phase continuously removed using a Dean Stark trap. A faster separation was observed and the organic layer was observed to appear less hazy. Solvent was removed from the organic phase by distillation. Results of NMR analysis of the organic phase following washing with IOA and distillation are presented in Table 2.

For EX-2 to EX-4, the procedure described for EX-1 was carried out, with the exception that flow rate of the reactant streams was varied to achieve the retention times indicated in Table 1. Composition of the organic phase by NMR after washing with IOA and distillation was not measured.

TABLE 1

| | Example Number | | | |
|---|---|---|---|---|
| | EX-1 | EX-2 | EX-3 | EX-4 |
| Retention Time | 5 min. | 10 min. | 15 min. | 20 min. |
| Reactor Temperature | 53° C. | 49° C. | 50° C. | 49° C. |
| Results of GC analysis of Organic Phase | | | | |
| % Composition 4-hydroxybenzophenone acrylate (ABP) | 95% | 97% | 96.6% | 96.3% |
| % Composition BP | 5% | 3% | 3.4% | 3.7% |

TABLE 1-continued

| | Example Number | | | |
|---|---|---|---|---|
| | EX-1 | EX-2 | EX-3 | EX-4 |
| Results of NMR analysis of Organic Phase | | | | |
| ABP | 97.5% | 97.4% | 96.6% | 96.4% |
| BP | 2.4% | 2.6% | 3.4% | 3.6% |
| mol % TEA | 0% | 0% | 0% | 0% |
| mol % TEA salt | 0.8% | 1.0% | 1.3% | 1.4% |
| mol % Acrylic Acid | 6.3% | 5.3% | 3.9% | 1.3% |
| mol % EtOAc | 71.7% | 71.0% | 71.0% | 72.8% |

TABLE 2

Results of NMR analysis of EX-1 organic phase after washing with aqueous IOA solution and distillation

| | |
|---|---|
| % Composition ABP | 97.5% |
| % Composition BP | 2.5% |
| mol % TEA | 0% |
| mol % TEA-salt | 0% |
| mol % AA | 0% |
| mol % EtOAc | 45.6% |
| mol % IOA | 37.1% |

Examples 5 Through 12 (EX-5 Through EX-11) and Counter Examples 1 and 2 (CE-1 and CE-2)

For EX-5 through EX-12, CE-1, and CE-2, the procedure described for EX-1 was carried out, with the exception that 30 g of the reaction product from the flow reactor was mixed with the acrylates indicated in Table 3, below. The time (in sec) after mixing for the phase split to be observed, as well as the observation of the quality of the phase separation, are indicated in Table 3. The quality of phase separation was noted as either "fair" or "excellent" based on visual observation. "Fair" indicates that two phases were observed but that the phase boundary was either not clearly visible or not sharp. "Excellent" indicates two phases were observed and the boundary between the two phases was clearly visible and sharp.

TABLE 3

Results of observation of phase separation after washing with acrylates and water.

| Example or Counter Example | Acrylate | Time (sec) | Phase Separation |
|---|---|---|---|
| EX-5 | 2 EHA | 10 | Excellent |
| EX-6 | BA | 15 | Excellent |
| EX-7 | BMA | 15 | Excellent |
| EX-8 | IOA | 15 | Excellent |
| EX-9 | PHA | 15 | Excellent |
| EX-10 | 2 OA | 20 | Excellent |
| EX-11 | 2 EHMA | 20 | Excellent |
| EX-12 | THFA | 60 | Excellent |
| CE-1 | LMA | >100 | Fair |
| CE-2 | C18 | >100 | Fair |

What is claimed is:

1. A method of making a benzophenonyl (alk)acrylic ester or substituted benzophenonyl (alk)acrylic ester comprising adding to a mixing chamber of a microflow reactor
   a benzophenone alcohol or substituted benzophenone alcohol comprising at least one hydroxy moiety,
   one or more bases that are sufficient to at least partially deprotonate the benzophenone alcohol or substituted benzophenone alcohol,
   a polar liquid,
   an (alk)acryloyl halide or 3-haloalkylcarboxyl halide, and
   an organic liquid that is immiscible with the polar liquid in a sufficient amount to dissolve the (alk)acryloyl halide or 3-haloalkylcarboxyl halide, wherein
   the molar flow ratio of all of the hydroxy moieties to the sum of all of the one or more bases is 1 to at least 1.1; and
   producing a product stream comprising one or more benzophenonyl (alk)acrylic ester or substituted benzophenonyl (alk)acrylic ester and one or more salts of the one or more bases; and wherein
   the polar liquid added to the mixing chamber is sufficient to dissolve the one or more salts; and
   the product stream has an organic portion and a polar portion, the organic portion of the product stream comprising the benzophenonyl (alk)acrylic ester or substituted benzophenonyl (alk)acrylic ester in an amount of at least 80 wt % based on the total weight of the benzophenonyl (alk)acrylic ester or substituted benzophenonyl (alk)acrylic ester, unreacted benzophenone alcohol or substituted benzophenone alcohol, and organic byproducts in the product stream; and further wherein either
   (a) the organic liquid comprises a compound of Formula (I); or
   (b) the method further comprises adding a compound of Formula (I) to the product stream; or
   (c) the organic liquid comprises a compound of Formula (I) and the method further comprises adding a compound of Formula (I) to the product stream

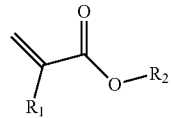

Formula (I)

wherein
$R_1$ is H or C1 to C4 alkyl; and
$R_2$ is C1 to C12 alkyl optionally interrupted by one or more O atoms.

2. The method of claim 1, wherein the organic liquid comprises a compound of Formula (I).

3. The method of claim 1, wherein the polar liquid comprises water.

4. The method of claim 1, wherein the molar flow ratio of the benzophenone alcohol or substituted benzophenone alcohol to the (alk)acryloyl halide or 3-haloalkylcarboxyl halide is 1 to at least 1.1.

5. The method of claim 1, wherein the mixing chamber of the microflow reactor is not cooled by cooling equipment.

6. The method of claim 1, wherein the mixing chamber of the microflow reactor comprises an exit port; and
   wherein the method further comprises a step of removing the (alk)acrylic ester from the exit port simultaneously with the adding step.

7. The method of claim 1, wherein the one or more bases comprises at least one of triethyl amine, dimethyl amine, trimethyl amine, methyldiethyl amine, alkali metal hydroxide, and alkali earth metal hydroxide.

8. The method of claim 1, wherein the (alk)acryloyl halide or a 3-haloalkylcarboxyl halide is 3-chloropropionylchloride.

9. The method of claim 1, wherein the (alk)acryloyl halide or a 3-haloalkylcarboxyl halide is an (alk)acrylyl halide.

10. The method of claim 1, wherein the (alk)acryloyl halide or a 3-haloalkylcarboxyl halide is acryloyl chloride or methacryloyl chloride.

11. The method of claim 1, wherein the mixing chamber of the microflow reactor has an internal volume of no more than 1 mL.

12. The method of claim 1, further comprising a step of adding water to the product stream.

13. The method of claim 1, wherein the polar portion is continuously separated from the organic portion of the product stream.

14. The method of claim 1, wherein in the compound of Formula (I), $R_1$ is H or methyl and $R_2$ is C1-C12 alkyl or tetrahydrofuranyl.

15. The method of claim 1, wherein the compound of Formula (I) is methyl methacrylate, butyl acrylate, tetrahydrofuranyl acrylate, 2-ethyl hexyl acrylate, and 2-methyl heptyl acrylate.

* * * * *